(12) United States Patent
Reiner

(10) Patent No.: US 7,421,647 B2
(45) Date of Patent: Sep. 2, 2008

(54) GESTURE-BASED REPORTING METHOD AND SYSTEM

(76) Inventor: Bruce Reiner, 6 Greenleaf Rd., Seaford, DE (US) 19973

( * ) Notice: Subject to any disclaimer, the term of this patent is extended or adjusted under 35 U.S.C. 154(b) by 0 days.

(21) Appl. No.: 11/176,427

(22) Filed: Jul. 8, 2005

(65) Prior Publication Data

US 2006/0007188 A1    Jan. 12, 2006

Related U.S. Application Data

(60) Provisional application No. 60/586,415, filed on Jul. 9, 2004.

(51) Int. Cl.
*G06F 17/00* (2006.01)
(52) U.S. Cl. ...................... 715/230; 600/407
(58) Field of Classification Search ............... 715/512, 715/230; 600/407; 345/619; 705/2
See application file for complete search history.

(56) References Cited

U.S. PATENT DOCUMENTS

| | | | |
|---|---|---|---|
| 4,974,194 A * | 11/1990 | Barker et al. ............... 715/540 |
| 5,148,366 A | 9/1992 | Buchanan et al. |
| 5,267,155 A | 11/1993 | Buchanan et al. |
| 5,522,022 A * | 5/1996 | Rao et al. ................... 345/440 |
| 5,586,239 A * | 12/1996 | Ueda .......................... 715/513 |
| 5,734,915 A * | 3/1998 | Roewer ....................... 715/512 |
| 5,768,418 A * | 6/1998 | Berman et al. .............. 382/187 |
| 5,782,762 A | 7/1998 | Vining |
| 5,832,474 A * | 11/1998 | Lopresti et al. ................ 707/2 |
| 5,838,313 A * | 11/1998 | Hou et al. ................ 715/500.1 |
| 5,884,256 A * | 3/1999 | Bennett et al. .............. 704/235 |
| 5,890,177 A * | 3/1999 | Moody et al. ............... 715/511 |
| 5,893,126 A * | 4/1999 | Drews et al. ................ 715/512 |
| 5,897,648 A * | 4/1999 | Henderson .................. 715/530 |
| 5,920,317 A * | 7/1999 | McDonald .................. 715/853 |
| 5,924,074 A * | 7/1999 | Evans ............................ 705/3 |
| 6,041,335 A * | 3/2000 | Merritt et al. ............... 715/512 |
| 6,057,845 A * | 5/2000 | Dupouy ...................... 715/863 |
| 6,058,322 A * | 5/2000 | Nishikawa et al. .......... 600/408 |

(Continued)

OTHER PUBLICATIONS

Caruso et al.,"Image Annotation with Adobe Photoshop", Journal of Digital Imaging, Dec. 2002, pp. 197-202.*

(Continued)

*Primary Examiner*—Doug Hutton
*Assistant Examiner*—James H Blackwell
(74) *Attorney, Agent, or Firm*—Jean C. Edwards, Esq.; Akerman Senterfitt

(57) ABSTRACT

The present invention is directed to gesture-based reporting system and method, which includes a client computer with high-resolution image displaying device, and an input device which is a programmable stylus, where the predetermined information contained within the report is defined by a series of symbols or gestures, which are drawn directly onto the image displayed on the image displaying device, using the programmable stylus. The gestures or symbols used, utilize an economy of symbols that are diverse in nature and have broad based appeal to the population of end users. At the same time, they can be made applicable to a variety of different specific situations, modalities, pathologies, etc., in order to interpret the imaging study. Therefore, unlike a traditional text report (where the image and text report are distinct and separate from one another), the informational content contained within the image and the gesture-based report are inseparable.

59 Claims, 4 Drawing Sheets

U.S. PATENT DOCUMENTS

| | | | |
|---|---|---|---|
| 6,083,162 A | 7/2000 | Vining | |
| 6,122,539 A * | 9/2000 | Figueira et al. | 600/411 |
| 6,366,683 B1 | 4/2002 | Langlotz | |
| 6,434,262 B2 * | 8/2002 | Wang | 382/132 |
| 6,542,579 B1 | 4/2003 | Takasawa | |
| 6,567,549 B1 | 5/2003 | Marianetti, II et al. | |
| 6,601,055 B1 * | 7/2003 | Roberts | 706/45 |
| 6,681,372 B2 * | 1/2004 | Yajima | 715/541 |
| 6,687,404 B1 * | 2/2004 | Hull et al. | 382/226 |
| 6,687,876 B1 * | 2/2004 | Schilit et al. | 715/512 |
| 6,694,163 B1 | 2/2004 | Vining | |
| 6,721,452 B2 | 4/2004 | Confer et al. | |
| 6,738,053 B1 * | 5/2004 | Borgstrom et al. | 345/179 |
| 6,901,277 B2 * | 5/2005 | Kaufman et al. | 600/407 |
| 6,915,265 B1 * | 7/2005 | Johnson | 705/2 |
| 6,988,990 B2 * | 1/2006 | Pan et al. | 600/437 |
| 7,053,916 B2 * | 5/2006 | Kobayashi et al. | 345/633 |
| 7,065,705 B1 * | 6/2006 | Wang et al. | 715/512 |
| 7,111,230 B2 * | 9/2006 | Euchner et al. | 715/512 |
| 7,120,299 B2 * | 10/2006 | Keskar et al. | 382/187 |
| 2002/0070970 A1 | 6/2002 | Wood et al. | 345/766 |
| 2002/0078088 A1 * | 6/2002 | Kuruoglu et al. | 707/512 |
| 2002/0109737 A1 * | 8/2002 | Jaeger | 345/863 |
| 2002/0131625 A1 | 9/2002 | Vining et al. | |
| 2003/0004991 A1 * | 1/2003 | Keskar et al. | 707/512 |
| 2003/0110178 A1 | 6/2003 | Woods et al. | |
| 2003/0147099 A1 * | 8/2003 | Heimendinger et al. | 358/462 |
| 2003/0190064 A1 * | 10/2003 | Inoue | 382/128 |
| 2004/0039987 A1 * | 2/2004 | Coppin et al. | 715/502 |
| 2004/0049543 A1 * | 3/2004 | Kaminsky et al. | 709/204 |
| 2004/0078215 A1 * | 4/2004 | Dahlin et al. | 705/2 |
| 2004/0085443 A1 * | 5/2004 | Kallioniemi et al. | 348/135 |
| 2004/0205542 A1 * | 10/2004 | Bargeron et al. | 715/512 |
| 2004/0207661 A1 * | 10/2004 | Akaki | 345/764 |
| 2004/0263662 A1 * | 12/2004 | Okisu et al. | 348/333.02 |
| 2005/0175245 A1 * | 8/2005 | Suntanto et al. | 382/229 |
| 2005/0289472 A1 * | 12/2005 | Morita et al. | 715/757 |
| 2006/0061595 A1 * | 3/2006 | Goede et al. | 345/619 |
| 2006/0150079 A1 * | 7/2006 | Albornoz et al. | 715/512 |
| 2007/0022371 A1 * | 1/2007 | Bargeron | 715/512 |

OTHER PUBLICATIONS

Caruso et al.,"Image Editing with Adobe Photoshop 6.0", Dept. of Radiology, Univ. of Louisville, 2002 pp. 993-1002.*

Mulhem et al.,"Advances in Digital Home Photo Albums", unknown copyright, pp. 1-27.*

Goede et al.,"A Methodology and Implementation for Annotating Digital Images for Context-Appropriate Use in an Academic Health Care Environment", JAMIA Jul. 27, 2003, pp. 29-41.*

* cited by examiner

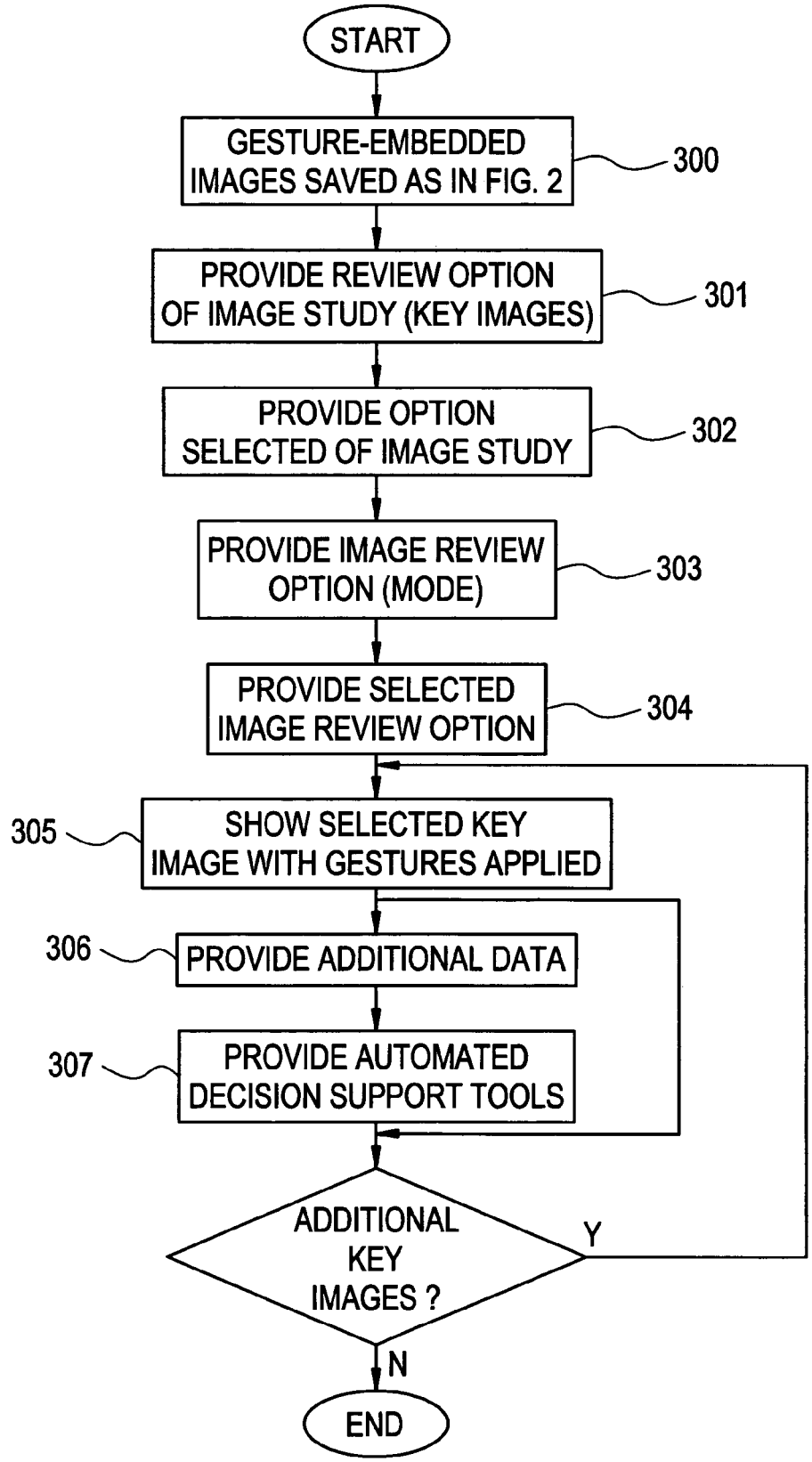

GESTURE-BASED REPORTING METHOD AND SYSTEM

CROSS-REFERENCE TO RELATED APPLICATIONS

The present application claims priority from U.S. Patent Provisional Application No. 60/586,415, filed Jul. 9, 2004, the contents of which are herein incorporated by reference in their entirety.

BACKGROUND OF THE INVENTION

1. Field of the Invention

The present invention relates to an image reporting method and system, and more particularly, to a gesture-, symbol- or icon-based method and system of reporting findings in a radiological environment.

2. Detailed Description of the Relevant Art

The image reporting methods and systems used in the medical field, particularly radiology, has involved radiologists making notes or marks with wax crayon on x-ray film, the marks which are erasable, inconsistent, and not reproducible. However, it has taken days for a typist and the radiologist to generate reports using this technique, and if a large volume of reports are generated, this technique has not been timely or accurate.

Another image reporting method which is used conventionally, involves a radiologist dictating a report into a microphone after reviewing and interpreting findings contained within a medical image. The dictated report is then transcribed by either a typist, or by a computer using speech recognition software.

In either approach, the input is speech generated, which is then converted into a text report. However, the drawback of this approach is a potential lack of accuracy due to the problems in the inscription of varying speech patterns.

Further, traditional reporting strategies require the user to divert attention from the image in order to perform ancillary tasks such as image navigation, processing, manipulation, and reporting (most commonly using a computer keyboard or mouse as the input device).

Thus, a method and system which performs all of these tasks in a timely and accurate fashion, and which can combine any of these tasks for efficiency purposes, is desired.

SUMMARY OF THE INVENTION

The present invention relates to a gesture-based reporting system and method, which includes a client computer or workstation with high-resolution image displaying device, and an input device which is a programmable stylus or electronic pen, where the individual concepts (i.e., radiological findings) contained within the report are defined by a series of symbols, icons, or gestures, which are drawn directly onto the image displayed on the image displaying device, by the radiologist, using the programmable stylus.

The symbols, such as checkmarks, dots, etc., are gestures or symbols which are predetermined to mean certain information. The gestures or symbols used, utilize an economy of symbols that are diverse in nature and have broad based appeal to the population of end users. At the same time, they can be made applicable to a variety of different specific situations, modalities, pathologies, etc., in order to interpret the imaging study.

Therefore, unlike a traditional text report (where the image and text report are distinct and separate from one another), the informational content contained within the image and the gesture-based report are inseparable. Instead of translating a finding or concept (i.e., an enlarged heart in a radiological application) from the image into text, the concept is retained directly within the image. This avoids the potential clerical and cognitive error, which can occur in the translational process from image to text.

By coupling imaging data, findings, and the report into one dataset, the present invention offers a unique ability to incorporate specialized decision support tools directly into the image and report simultaneously. Using a standardized and universally accepted gesture language, potential misperceptions are alleviated, and language barriers are no longer a problem.

The computer program that implements the gesture-based reporting, can perform the function of storing the image with the gestures thereon. Further, the gesture language used to map to specific findings and concepts are recognized by the gesture recognition software program, and these findings and concepts can be translated into a report using the gestures. Still further, the type of image would also be recognized by the computer program, and the computer program would be able to generate an image and place the symbols onto the selected image in the appropriate areas. Thus, the present invention works bi-directionally.

The bi-directional nature of the present invention allows for a traditional prose report to be converted into a gesture report, using natural language processing (NLP) to convert prose into symbols. This could be performed in a retrospective fashion to convert historical prose reports into gesture-based reports—providing direct comparison of reports between different users in a standardized reporting format.

In another embodiment consistent with the present invention, detailed and descriptive information (relative to the described finding) can be provided by incorporating additional modifying terms and descriptors into the gesture language, in a highly structured and organized fashion. These modifiers and descriptors force the user to identify and quantify his analysis in pre-defined and limited terms, obviating the uncertainty of the traditional prose format which may be flowery, lengthy, and unclear as to the significance and exact findings being described.

The reporting format of the gesture-based reporting method and system supplements the traditional text reports, and can add more flexibility to the user. Thus, the various reports generated can be electively turned on or off by the user of the system, and can include: 1) gestures or symbols alone embedded on the image, which map to specific findings and concepts, according to the present invention; 2) an itemized list of findings (and modifying terms associated with each finding), in a structured, text format; and 3) a traditional text report with the findings translated into prose format using natural language processing (NLP) tools.

The gesture-based report and the gesture-embedded images or "key images", can then be auto-routed to the referring clinician using a pre-defined communication protocol.

The advantages of using gesture-based reporting when compared to conventional reporting schemes, include the important advantage that the user never takes their eye off the target image, thereby maintaining continuous contact with the object of focus. This offers a number of theoretical advantages in eye tracking, workflow, and diagnostic accuracy.

In one embodiment consistent with the present invention, the present invention may utilize an input device such as a programmable stylus, which can perform ancillary tasks such as image navigation, processing, manipulation, and reporting, using the stylus as a combined input and navigational device. This programmable stylus can not only be used to draw symbols onto the image, but can also accomplish other tasks intrinsic to the image display, navigation, interpretation, and reporting processes that are superior to using traditional computer keyboard or mouse methods. This would allow image navigation and display to be a continuous process, whereby the user never takes their eyes off the image—enhancing productivity and workflow, and also improving the image perceptual process.

The creation of structured reporting using a standardized gesture language allows for the creation of a referenceable database, which can be queried by the user for research purposes. This creates a valuable resource for practice management, clinical research, quality assurance, or utilization review.

In another embodiment consistent with the present invention, interactive consultation can be performed, with the end-user having the ability to "turn on and turn off" the embedded gestures or symbols, such that the combined image/report provides becomes an electronic consultative tool between two users. This improves on the present methods where users have to move from the images (and the findings contained within them) to the report, which are decoupled and separate from one another.

In another embodiment consistent with the present invention, neural networks can be used to more accurately define image interpretation where users are inconsistent in the results of their analysis.

Finally, with gesture-based reporting, varying overlays or tiers of reports can be provided, which can show either different findings over time, or different aspects of the findings, thereby providing as much information to a user as possible in one image.

There has thus been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

BRIEF DESCRIPTION OF THE DRAWINGS

FIG. 4 is a flowchart showing the bi-directional electronic consultation embodiment of the gesture-based reporting method and system of the present invention.

DETAILED DESCRIPTION OF THE INVENTION

The present invention relates to an alternative approach to creating an image-based report. Applications of this gesture-based (or symbol-based or icon-based) reporting can be utilized for any type of image-reporting that would benefit from a "shorthand" that is accurate and descriptive, such as in the fields of medicine (i.e., radiology), landscaping, architecture, etc.

However, the medical (i.e., radiology) application will be the exemplary embodiment as discussed below. In the exemplary radiological application, the present invention includes a computer-implemented method and computer system function to create a database of gesture-embedded image reports from which text reports can be generated and from which data mining and other analyses can be conducted.

Although the method and system of the present invention is described as being directed to the analysis of digital images, the present invention can also be adapted for use with analog images such as conventional x-ray films, photographs, or paper-based images.

Figure 1:
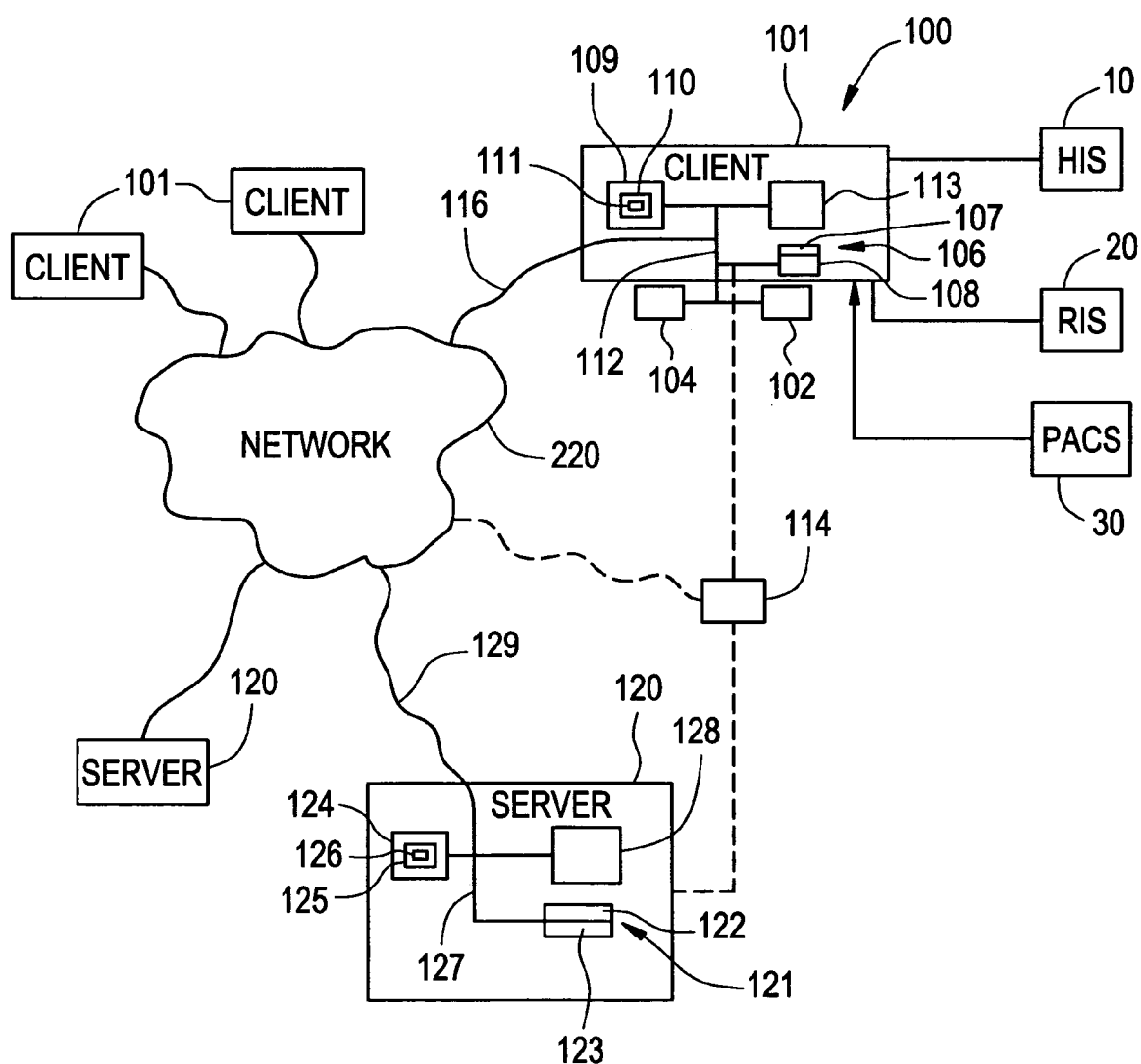
FIG. 1 is a schematic showing the gesture-based reporting method and system according to one embodiment consistent with the present invention.

In the exemplary embodiment of medical (radiological) applications, the reporting system 100 of the present invention (see FIG. 1) is also designed to interface with existing information systems such as a Hospital Information System (HIS) 10, a Radiology Information System (RIS) 20, a Picture Archiving and Communication System (PACS) 30, and to conform with the relevant standards, such as the Digital Imaging and Communications in Medicine (DICOM) standard, DICOM Structured Reporting (SR) standard, or the Radiological Society of North America's Integrating the Healthcare Enterprise (IHE) initiative.

Thus, bi-directional communication between the gesture-based reporting system 100 of the present invention and the information systems, such as the HIS 10, RIS 20, and PACS 30, etc., allows the reporting system 100 to retrieve information from these systems and update information therein and provide the desired report generated by the reporting system 100.

The reporting system 100 of the present invention (see FIG. 1) includes a client computer 101, such as a PC, which may or not be interfaced or integrated with the PACS 30, and includes an imaging display device 102 capable of providing high resolution of digital images in 2-D or 3-D, for example. However, if the image resolution can be sufficiently high, the client may be a mobile terminal, such as a mobile computing device, or a mobile data organizer (PDA), operated by the user accessing the program remotely from the client (see FIG. 2).

Methods and systems consistent with the present invention are carried out by providing an input means 104 (see FIG. 1), or user selection means, including hot clickable icons etc., or selection buttons, in a menu, dialog box, or a roll-down window of an interface provided at the client 101, and the user may input commands through a programmable stylus, keyboard, mouse, speech processing means, laser pointer, touch screen, or other input means 104.

The input or selection means 104 may be constituted by a dedicated piece of hardware or its functions may be executed by code instructions executed on the client processor 106, involving the display unit 102 for displaying the selection window and a stylus or keyboard for entering a selection, for example.

However, input of the gestures, symbols, or icons, by a user would preferably be accomplished using a multi-functional, programmable stylus 104, which can not only be used to draw symbols onto the image, but can also accomplish other tasks intrinsic to the image display, navigation, interpretation, and reporting processes that are superior to using traditional computer keyboard or mouse methods (both within the PACS and Electronic Medical Report (EMR)).

The client 101 typically includes a processor 106 as a client data processing means, the processor including a central processing unit (CPU) 107 or parallel processor and an input/output (I/O) interface 108, a memory 109 with a program 110 having a data structure 111, all connected by a bus 112. Further, the client 101 would include an input device or means 104, a display 102, and may also include one or more secondary storage devices 113. The bus 112 may be internal to the client 101 and may include an adapter to a keyboard or input device 104 or may include external connections.

The imaging display device 102 for the present invention is a high resolution touch screen computer monitor, which would allow images, such as x-rays, to be readable and for the gestures or symbols to be applied easily and accurately. Alternatively, the imaging display device 102 can be other touch sensitive devices including tablet, pocket PC, and plasma screens. The touch screen would be pressure sensitive and responsive to the input of the stylus 104 which would be used to draw the gestures or symbols of the present invention, directly onto the image displaying device 102.

In addition, high resolution goggles may be used to provide end users with the ability to review images without the physical constraints of an external computer. For example, a surgeon wearing specialized high resolution goggles to display the cross-sectional radiological image of a brain tumor in 3-D format, would be able to note the gestures on the image highlighting the pathology in question and reporting pertinent characteristics (i.e., anatomic localization, size, etc.), to serve as a guide during surgery. These goggles are used for image-guided surgery and gesture-based reporting would serve to provide consultation on pertinent findings during the course of surgery.

In another example, an internal medicine physician could use these specialized goggles outside the hospital, to review images with embedded gestures or symbols. The images could be downloaded using wireless technology and displayed on the goggles, thereby eliminating the need for a computer screen for image display.

Note that with respect to the client system 101, the graphics user interface is a client application written to run on existing computer operating systems which may be ported to other personal computer (PC) software, personal digital assistants (PDAs), and cell phones, and any other digital device that has a screen or visual component and appropriate storage capability.

The processor 106 at the client 101 may be internal or external thereto, and executes a program 110 adapted to predetermined operations. The processor 106 has access to the memory 109 in which may be stored at least one sequence of code instructions comprising the program 110 and the data structure 111 for performing predetermined operations. The memory 109 and program 110 may be located within the client 101 or external thereto.

Note that at times the system of the present invention is described as performing a certain function. However, one of ordinary skill in the art would know that the program 110 is what is performing the function rather than the entity of the system itself.

The program 110 which runs the gesture-based reporting method and system of the present invention can include a separate program code for performing a desired operation, or may be a plurality of modules performing sub-operations of an operation, or may be part of a single module of a larger program 110 providing the operation.

The processor 106 may be adapted to access and/or execute a plurality of programs 110 corresponding to a plurality of operations. An operation rendered by the program 110 may be, for example, supporting the user interface, data mining functions, performing e-mail applications, etc.

The data structure 111 may include a plurality of entries, each entry including at least a first storage area that stores the databases or libraries of gesture symbols, or image files, for example.

The storage device 113 stores at least one data file, such as image files, text files, data files, audio, video files, etc., in providing a particular operation. The data storage device as storage means 113, may for example, be a database, including a distributed database connected via a network, for example. The database can be a computer searchable database and may be a relational database. The storage device may be connected to the server 120 and/or the client 101, either directly or through a communication network, such as a LAN or WAN. An internal storage device 113, or an external storage device 114 is optional, and data may also be received via a network and directly processed.

In methods and system consistent with the present invention, the client 101 may be connected to other clients 101 or servers 120, including administration, billing or other systems, via a communication link 116 as a client communication means, using a communication end port specified by an address or a port, and the communication link 116 may include a mobile communication link, a switched circuit communication link, or may involve a network of data processing devices such as a LAN, WAN, the Internet, or combinations thereof. In particular, the communication link may be to e-mail systems, fax, telephone, wireless communications systems such as pagers and cell phones, wireless PDA's and other communication systems.

The communication link 116 may be an adapter unit capable to execute various communications protocols in order to establish and maintain communication with the server 120, for example. The communication link 116 may be constituted by a specialized piece of hardware or may be realized by a general CPU executing corresponding program instructions. The communication link 116 may be at least partially included in the processor 106 executing corresponding program instructions.

In one embodiment consistent with the present invention, if a server 120 is used in a non-distributed environment, the server 120 would include a processor 121 having a CPU 122 or parallel processor which is a server data processing means, and an I/O interface 123, but may also be constituted by a distributed CPU 122 including a plurality of individual processors 121 on one or a plurality of machines. The processor 121 of the server 120 may be a general data processing unit, but preferably a data processing unit with large resources (i.e., high processing capabilities and a large memory for storing large amounts of data).

The server 120 also includes a memory 124 with program 125 having a data structure 126 all connected by a bus 127. The bus 127 or similar connection line can also consist of external connections, if the server 120 is constituted by a distributed system. The server processor 121 may have access to a storage device 128 for storing preferably large numbers of programs for providing various operations to the users.

The data structure 126 may include a plurality of entries, each entry including at least a first storage area which stores image files, for example, but may also have alternative embodiments including that associated with other stored information as one of ordinary skill in the art would appreciate.

The server 120 may be a single unit or may be a distributed system of a plurality of servers 120 or data processing units, and may be shared by multiple users in direct or indirect connection to each other. The server 120 performs at least one server program for a desired operation, which is required in serving a request from the client 101.

The communication link 129 from the server 120 is preferably adapted to communicate with a plurality of clients.

The present invention is implemented in software which can be provided in a client and server environment, or in a distributed system over a computerized network across a number of client systems. Thus, in the present invention, a particular operation may be performed either at the client or the server, at the edge of a network or at the center, or both. Therefore, at either the client or the server, or both, corresponding programs for a desired operation/service are available.

In a client-server environment, at least one client and at least one server are each connected to a network 220 such as a Local Area Network (LAN), Wide Area Network (WAN), and/or the Internet, over a communication link 116, 129. Further, even though the systems HIS 10 and RIS 20, and PACS 30 (if separate) are shown as directly connected to the client 101, it is known that these systems could be connected to the client over a LAN, WAN, and/or the Internet via communication links. Interaction with users may be through secure and non-secure internet connectivity. Thus, the steps in the methods consistent with the present invention are carried out at the client or at the server, or at both, the server (if used) being accessible by the client over for example, the Internet using a browser application or the like.

The client system 101 may include communications via a wireless service connection. The server system 120 may include communications with network/security features, via a wireless server, which connects to, for example, voice recognition. However, one of ordinary skill in the art would know that other systems may be included.

In another embodiment consistent with the present invention, the client system may be a basic system, and the server may include all of the components necessary to support the software platform of the present invention. Further, the present client-server system may be arranged such that the client system can operate independently of the server system, but that the server system can be optionally connected. In the former situation, additional modules would instead be connected to the client system. In another embodiment consistent with the present invention, the client system and server system can be disposed in one system, rather being separated into two systems.

Although the above physical architecture has been described above as client-side or server-side components, one of ordinary skill in the art would know that the above components of the physical architecture may be in either client or server, or in a distributed environment.

Further, although the above-described features and processing operations may be realized by dedicated hardware, or may be realized as programs including code instructions executed on data processing units, it is further possible that parts of the above sequence of operations are carried out in hardware, whereas other of the above processing operations are carried out using software.

The underlying technology allows for replication to various other sites. Each new site can maintain "state" with its neighbors so that in the event of a catastrophic failure, other server systems can continue to keep the application running, and allow the system to load-balance the application geographically as required.

Further, although aspects of one implementation of the present invention are described as being stored in memory, one of ordinary skill in the art will appreciate that all or part of the methods and systems consistent with the present invention may be stored on or read from other computer-readable media, such as secondary storage devices, like hard disks, floppy disks, CD-ROM, a carrier wave received from a network such as the Internet, or other forms of ROM or RAM either currently known or later developed. Further, although specific components of the system have been described, one skilled in the art will appreciate that the system suitable for use with the methods and systems consistent with the present invention, may contain additional or different components.

Accordingly, in one embodiment consistent with the present invention, the gesture-based reporting system 100 and method as used in an exemplary radiology method and system, includes a client computer 101 with image displaying device 102, and an input device 104 which is a programmable stylus. The programmable stylus 104 is used as input means, and can not only be used to draw symbols onto the image, but can also accomplish other tasks intrinsic to the image display, navigation, interpretation, and reporting processes of the present invention.

Thus, the radiologist turns on the client computer system 101, which may be a stand-alone PC, or part of or connected to a client workstation known in the radiological field as the PACS workstation 30. In this exemplary embodiment, the client computer 101 is the PACS 30, and some or all of the present invention, with respect to imaging display device 102, computer memory 109 and program 110 etc., is contained within the PACS 30 instead of being provided separately.

Thus, the user logs onto the PACS system 30 once the client 101 is operational.

The computer program 110 will then offer the user a menu in step 200, and the radiologist can then select, and the program 110 will open up in step 201, the worklist folder listing image files available for analysis, from the menu offered.

In step 202, the radiologist can select and the computer program 110 will load the imaging study (i.e., patient data) selected in step 201, including but not limited to image data corresponding to radiological examinations of patients from the PACS 30, and additional information, including but not limited to laboratory data, pathology reports from the Electronic Medical Record (EMR), patient demographics, and billing, from data storage 113, onto the display 102. Note that the PACS 30 stores information according to existing standards such as DICOM. The data from the PACS 30 is stored in an examination image storage device 114, 128 for example, where it can be accessed via the client computer 101 for display on the image displaying device 102. Alternatively, the reporting system 100 can directly access the PACS images in storage 113 without the need for an intermediate storage device 114 or 128, for example.

The selected imaging study, including all of the associated unread (or read) examination files for that patient, is displayed by the computer program 110 on the client 101. The study can be organized by the computer program 110 by DICOM series prior to display.

When the study only contains a few images (radiography or mammography), the radiologist reviews the images in a static fashion. If the imaging study contains many images (CT, MRI), the images are reviewed in a dynamic fashion using a cine format (which is akin to a movie where the images rapidly scroll up and down in a sequential fashion).

Figure 3:
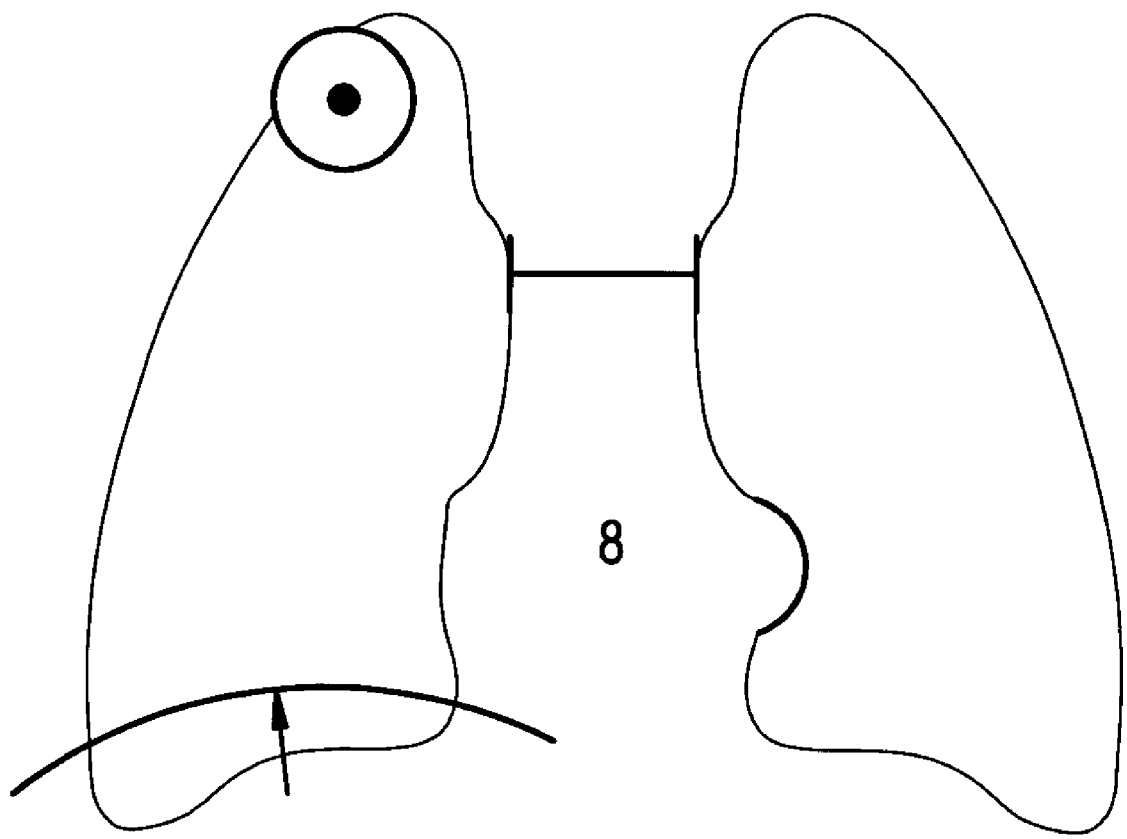
FIG. 3 is a depiction of a chest computed tomography (CT) of a person, showing gestures and modifiers on the image according to one embodiment consistent with the gesture-based reporting method and system of the present invention.

In step 203, the radiologist selects the desired image display format (static or dynamic) and begins reviewing the images. When the radiologist observes a pertinent finding, the specific image of interest is denoted (using the stylus 104) and marked as a "key image" using an appropriate gesture or symbol on the image (see FIG. 3). The radiologist draws the pre-defined symbol over the finding of record, based on an established gesture language, to create an "embedded" image.

The gestures or symbols (see Table 1), such as checkmarks, dots, etc., are gestures or symbols which are predetermined to mean a certain type of pathology. The gestures or symbols used utilize an economy of symbols that are diverse in nature and have broad based appeal to the heterogeneous population of end users (i.e., radiologists). At the same time, they are applicable to all imaging modalities, anatomic regions, and different types of pathology that the radiologists are asked to interpret in imaging studies.

For example, as shown in Table 1, a check mark can be used to show a "normal" image, an "S" shaped line through the long axis of the spine to show scoliosis, three dots forming a triangle to show airspace disease, three horizontally-oriented tacked lines to show interstitial disease, etc. However, it would be obvious to one of ordinary skill in the art that various different gestures, symbols or icons could be used to identify differing conditions and diseases, these gestures or symbols which would be taught to the radiologist beforehand, either in a text, or which may be provided in a tutorial on the client computer 101.

TABLE 1

| Description | Gesture | Description | Gesture |
|---|---|---|---|
| Normal | √ | Atalectasis | ╱ |
| Delete | X | Increasing | ↑ |
| Scoliosis | ʃ | Decreasing | ↓ |
| COPD | ⌒ (over diaphragm) | Pleural Effusion | ⊃ |
| Cardiomegaly | Ɔ (reverse letter "C") | Fracture | F |
| Airspace disease | ∴ | Surgery | 8 |
| Interstitial disease | ≡ | Widening | ⊢―⊣ (bracket) |
| Eltasia | ⌒) | Degenerative change | Δ |
| Nodule | ⊙ (circle around nodular density | Bulla/BLEB | B |

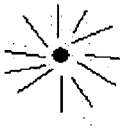

After the radiologist defines the primary finding, modifiers may be recorded on the image using the stylus 104 by the radiologist, also using pre-defined symbols and icons, an example of which are shown in Table 2. The modifying terms and descriptors force the radiologist to identify and quantify his analysis in pre-defined and limited terms, obviating the uncertainty of the traditional prose format which may be flowery, lengthy, and unclear as to the clinical significance and exact etiology of the findings being described.

For example, when the radiologist wants to specify the anatomic location of the lung nodule, he/she can, for example, "click" on the designated icon for "anatomy", and localizes the area of interest on the corresponding three-dimensional anatomic map using the stylus 104. These modifying gestures or symbols provide additional information regarding size, morphology, clinical significance, and diagnosis (see Table 2 and FIG. 3); although one of ordinary skill in the art would know that other symbols other than the ones shown, can be used for these and any other terms.

TABLE 2

| Modifying Term | Gesture | Modifying Term | Gesture |
|---|---|---|---|
| Level of diagnostic confidence |  (Rodin's Thinker) | Confidence in diagnosis |  |
| Level of clinical significance |  (doctor with mirror) | Measurements | 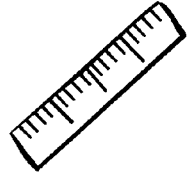 (ruler) |
| Time course/chronicity of finding |  | Morphology |  |
| Quality assurance indicator | Q | Follow up Recommendations |  |
| Education/Teaching FIE |  | Decision Support |  |
| Temporal Change |  | | |

After completion of image review and interpretation, the radiologist can then sign the gesture-embedded image by electronically placing his/her initials (using the stylus 104) on the image, for example in the lower right hand corner of one of the key images.

The image with the gestures and/or for the modifiers recorded thereon, can be saved on the client computer 101 in step 204.

After being instructed to "save", the computer program 110 will correlate the gesture or modifier recorded on the image, to a database 113, 114 or 128 for example, of gestures which provide the text for the correlation of the gesture or modifier, in step 205. The program 110 will then update the display 104 to show the text correlating to the gesture or modifier, next to the gesture or modifier symbol in step 206. The computer program 110 will offer confirmation and verification of the gestures or modifiers to be saved, by flashing the corresponding text for the entered gesture or symbol at the location of the gesture in step 207.

If the computer program misinterprets the gesture or symbol entered, and the text for the gesture or symbol is incorrect, the radiologist will place an "X", for example, over the gesture or symbol (for "delete"), and the computer program 110 in step 208, will erase or delete the text and/or the gesture or symbol for the image and the corresponding report related to that gesture.

The radiologist then re-enters the gesture-based symbol as in step 204, and repeats the process, eventually confirming the gesture when visualizing the correct corresponding text. The computer program 110 will confirm the text as correct in step 209, and then save the gesture-embedded image in step 210.

The "saved" annotated "key images" are stored separately in the database or archive 113, 114 or 128, for example, in addition to the comprehensive imaging dataset. These "key images" with the embedded gesture-based symbols can also be electronically sent directly to the referring clinician (based on a pre-defined communication protocol, such as e-mail, etc.) in step 211.

Once the image/report has been signed off and saved, the computer program 110 then brings up the radiology worklist folder and the radiologist can then click on a new image file and repeat the above process.

In another embodiment consistent with the present invention, if the radiologist is correlating with an historical comparison study and notices some previously reported findings remain, he/she can pull up a previous image, then either redraw the appropriate gestures or symbols or re-propagate gestures or symbols from the prior study by dragging the gestures over to the new study using the stylus 104. Thus, the computer program 110 will allow the movement of gestures from one image to another, in a similar fashion to a "copy" or "cut and paste" function in word processing.

In another embodiment consistent with the present invention, to facilitate the interpretation process, the radiologist can utilize automated decision support by clicking on the corresponding icon with the stylus 104. Examples of automated decision support include temporal subtraction (where changes over time are noted), computer-aided detection (CAD) (which detects pre-defined pathologies), computer-generated measurements and differential diagnosis (which provides a list of potential pathologies depending on the radiological findings). These automated decision support systems can provide findings which can be recorded onto the image in gestures, by the radiologist, or automatically translated into gestures, depending on how the automated decision support system works and can be integrated into the gesture-based reporting method and system of the present invention.

For example, a radiologist interpreting a chest CT for the presence of lung cancer can utilize computer-aided detection (CAD) software to assist in the interpretation process. In one embodiment consistent with the present invention, the CAD findings can be superimposed onto the image by the computer program 110 using a different color/format relative to the gesture-based reporting symbols. This allows for the clinician or radiologist to essentially "turn on and off" gesture-based reporting and CAD at their discretion. Images can be viewed with or without these "layers of data" and the entire dataset is permanently archived/stored in a collective fashion by the program 110.

In generating a report from the gesture-based reporting method and system, digital ink technology (i.e., electronically creating symbols and translating them into text) and specialized recognition software to translate the gestures or symbols used to map to specific radiological findings and concepts into an itemized text report, would be provided. The program 110 containing this recognition and report generation software is provided in the computer program 110 and in one embodiment consistent with the present invention, possibly integrated with the PACS which is responsible for image display, distribution, and storage (of both medical images and reports). Natural language processing (NLP) would provide the intelligence to convert the gestures and itemized text into a standard prose format.

Once the gesture-based symbols are embedded on the image, the report may be generated in at least three formats, as desired. In one embodiment consistent with the present invention, the reports generated using gesture based reporting formats can each be electively turned on or off by the user of the system, and include:

1) gestures or symbols alone embedded on the image, which map to specific findings and concepts, as in the present invention; or 2) an itemized list of findings (and modifying terms associated with each finding), in a structured, text format; or 3) a traditional text report with the findings translated into prose format using natural language processing (NLP) tools.

However, unlike the traditional reports, the creation of structured reporting using a standardized gesture language allows for the creation of a referenceable database (for example, storage 114), which can be queried for clinical and research purposes.

Therefore, unlike a traditional text report (where the image and text report are distinct and separate from one another), the informational content contained within the image and the gesture-based report are inseparable. Instead of translating a finding or concept (i.e., enlarged heart) from the image into text, the concept is retained directly within the image. This avoids the potential clerical and cognitive error, which can occur in the translational process from image to text.

Thus, by coupling imaging data, findings, and the report into one dataset, the present invention offers a unique ability to incorporate specialized decision support tools directly into the image and report simultaneously. For example, with traditional prose reporting, a great deal of ambiguity is introduced through the use of synonyms, which are commonly used to describe similar (but sometimes different) concepts. The clinical may have different clinical perceptions of the synonymous terms "infiltrate", "airspace disease", "consolidation" and "pneumonia". Using a standardized and universally accepted gesture language, these potential misperceptions are alleviated, and language barriers are no longer a problem.

Thus, in the aforementioned reference to "infiltrate", in one embodiment consistent with the present invention, the user can use the universal symbol for the finding and query the report database for all patients who had this reported finding between specific dates of time or who fulfilled certain demographic or clinical profiles. This creates a valuable resource for practice management, clinical research, quality assurance, or utilization review.

In addition, in one embodiment consistent with the present invention, a report can be used to generate an image which shows the specific findings detailed in the report. For example, the type of x-ray (i.e., chest, etc.) would be recognized by the computer program 110, and the computer program 110 would be able to generate an x-ray and place the gestures or symbols onto the selected film in the appropriate areas using a report as a basis. Thus, the present invention works bi-directionally.

The bi-directional nature of the present invention allows for a traditional prose report to be converted into a gesture report, using natural language processing (NLP) to convert prose into symbols. This could be performed in a retrospective fashion to convert historical prose reports into gesture-based reports—providing direct comparison of reports between different users in a standardized reporting format.

In another embodiment consistent with the present invention, interactive consultation can be conducted with the clinician. By embedding the findings directly into the medical image as in the present invention, and providing the end-user with the ability to "turn on and turn off" these embedded symbols, the combined image/report provides becomes an electronic consultative tool.

Figure 2:
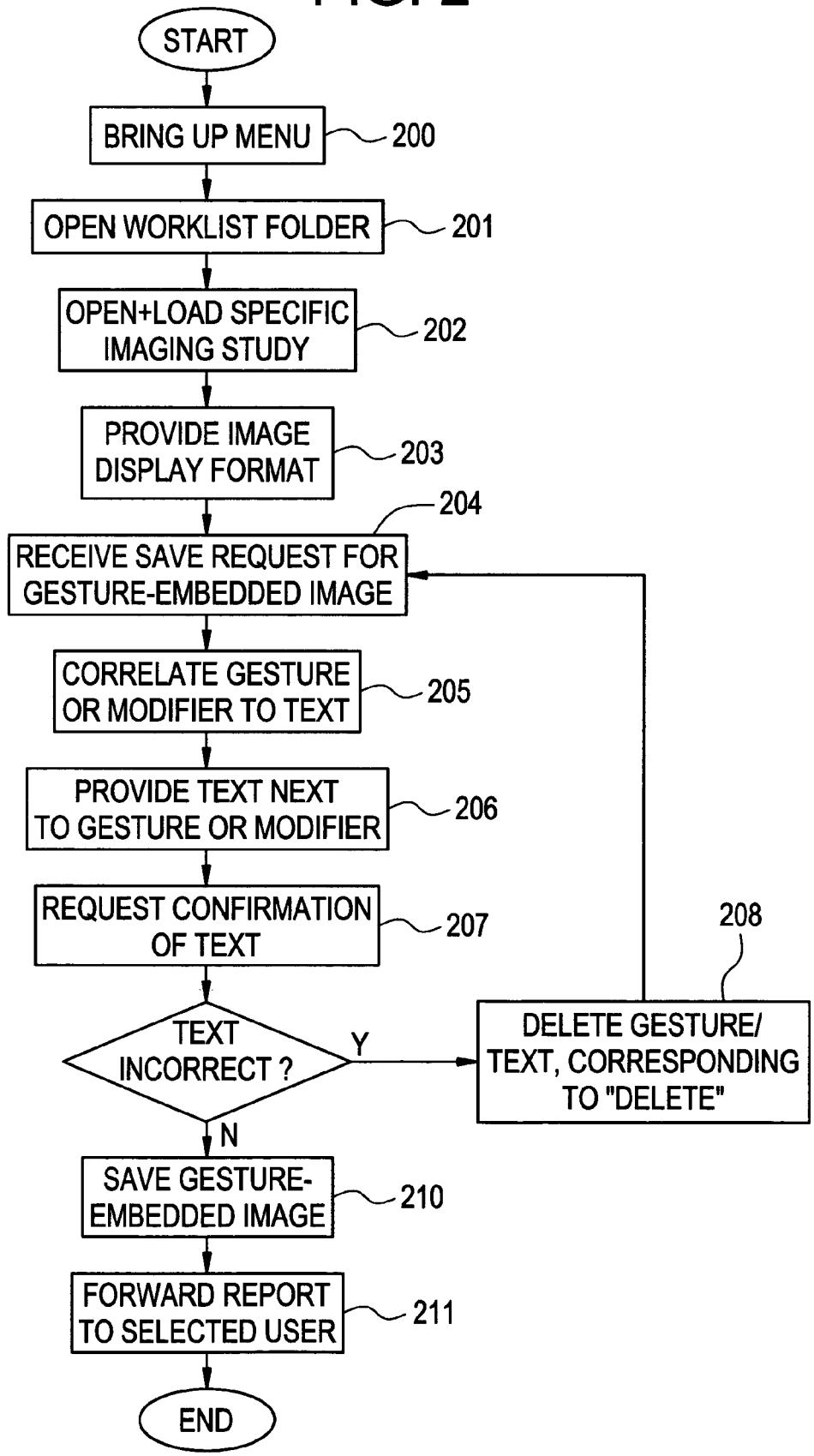
FIG. 2 is a flowchart showing the gesture-based reporting method according to one embodiment consistent with the present invention.

For example, in step 300 (see FIG. 4), the computer program 110 saves an embedded image that was interpreted by a radiologist who had reviewed a chest CT exam as previously described in FIG. 2, and who had made the following findings by embedding the appropriate gestures or symbols and modifiers onto the "key images".

1. Pulmonary embolism
2. Pneumonia
3. Pleural effusion
4. Hilar lymphadenopathy

When the clinician calls up the CT for review on the client computer 101, the computer program 110, in step 301, presents the user with the option to review the study in its entirety (from beginning to end, consisting of 600 individual images), or to review "key images" only (consisting of 4 images).

If the user elects to view "key images" only, the computer program 110 then presents the user in step 302 with the 4 "key images" in a pre-selected format based on the user preference. For clinician A, for example, this consists of all 4 images displayed on a single display or monitor 102 using a 4:1 display format, for example. For Clinician B, for example, the 4 individual images are displayed individually using a 1:1 display format, for example, with the clinician being able to navigate between images using the input device 104 of their own preference (i.e., stylus, track ball, mouse).

When the clinician highlights the first "key image" (once again using their desired input device 104), the computer program 110 presents the user with the option to review the image in, for example, three ways in step 303:

1. Image without symbols
2. Image with symbols (static mode)
3. Image with symbols (dynamic mode)

Note that in one embodiment consistent with the present invention, the clinician's individual preference can already be established in the computer program 110 as a default and incorporated into the computer sign-on process, but the clinician has the ability to override the program 110 default at any point in time. In addition, the clinician can toggle between the various options "on the fly" by activating the appropriate icon for that viewing mode manually, for example.

If, for example, the clinician has selected option 3 (image display with symbols using dynamic mode) as a default, the computer program 110 will present the highlighted "key image" with a sequential display of embedded symbols in step 304, in the exact order that the radiologist recorded them during interpretation. This in effect becomes an active movie, where the end-user views the entire interpretation process from beginning to end (and can control the speed, based on their preference).

In the example of the CT case, the first highlighted "key image" chosen by the clinician shows the pulmonary embolism in the exact viewing state that the radiologist was using at the time of symbol application. This entails a number of pre-selected variables including but not limited to, for example, the specific window/level setting employed, the magnification factor, the specific processing algorithm employed, the specific anatomic orientation (sagittal, axial, coronal), and any 3-D volume rendering used. In one embodiment consistent with the present invention, the pre-selected variables can be chosen prior to highlighting the key image by the user. The highlighting of the key image in step 305 creates a "short cut" for the clinician to avoid the time consuming process of image manipulation and allows the clinician to review the image in a manner identical to the interpreting radiologist.

The clinician then passively views the electronic consultation as gestures or symbols are automatically applied by the computer program 110 in step 305. In addition to the gestures or symbols themselves, the computer program 110 shows the clinician the corresponding text as each symbol is recognized by the computer program 110 gesture recognition software. This in effect has the advantage of creating an educational tool for gesture or symbol recognition for the clinician, being able to actively associate each applied gesture with its corresponding text.

After the gesture or symbol for pulmonary embolism is applied by the computer program 110, the clinician then sees the various modifying symbols applied by the program 110, which describe, for example, size (i.e., in linear or volumetric measurements), anatomic location (i.e., $2^{nd}$ order branch of the right upper lobe pulmonary artery), internal composition (i.e., non-calcified and occlusive), clinical significance (i.e., extremely high), and diagnostic level of confidence (i.e., high). Note that the gestures can be shown as being applied in the order that they were recorded, or can be shown all at once, depending on user selection.

In another embodiment consistent with the present invention, after completion of the entire sequence of symbol application (which typically takes 5-10 seconds) by the computer program 110, the clinician can then opt to view "additional data" by clicking an education icon "on" in step 306. The computer program 110 then presents the clinician with a number of resources including, for example, journal articles, web links, teaching file cases of related cases; using a search engine that search the databases based on the pre-defined user preferences.

Another option presented to the clinician by the computer program 110 in step 307 of one embodiment of the present invention, is the application of decision support tools (i.e., image processing, CAD, segmentation, differential diagnosis) which are, for example, customized to the reported findings and clinical indication, as well as the clinician's predetermined preferences, as noted above.

If the clinician opts not to review "additional data" then the electronic consultation of this image is terminated by the computer program in step 308, and the second highlighted "key image" is presented by the computer program in step 309, in this exemplary case, demonstrating the finding of pneumonia within the superior segment of the right lower lobe, which has decreased in overall volume by 20%, when compared with the comparison CT exam performed 5 days earlier.

This sequence by the computer program 110 is relatively short (approximately 5-10 seconds), and the computer program 110 follows with the presentation of the third and fourth highlighted "key images", after which, the electronic consultation is ended.

The entire sequence of events would take a short period of time—about 1-3 minutes, depending upon the options employed by the clinician. At any time during the consultation, the clinician can highlight a specific image or data point (using the stylus 104) and the program 110 will "save it" to be electronically sent to its own imaging folder, which can be accessed by predetermined factors, such as, for example, disease state, radiological finding, patient name, modality, etc.

The electronic consultation using the gesture-based reporting of the present invention is bidirectional in nature and the computer program 110 allows for the same sequence to be reviewed in reverse order, with the clinician doing the reporting first. In this exemplary instance, a clinician (i.e., ER physician) has reviewed the chest radiograph first (i.e., at 1:30 am) and recorded his/her preliminary interpretation using the appropriate gesture language. For example, the clinician has recorded the following symbols (in sequential order):

1. Density, poorly defined, right lower lobe, of uncertain clinical significance
2. Cardiomegaly, mild, minimal acute clinical significance
3. Degenerative changes, mid-thoracic spine, no acute clinical significance In this example, the radiologist interprets the same study at, for example, 8:00 am and reviews the ER physician's interpretation (which takes only a few seconds—i.e., 5-10 seconds) using the gesture-based reporting method. Additional data obtained by an automated search on the EMR states the patient's WBC count is normal and no fever is present.

In addition, in this example, the patient's imaging file includes a CT exam performed one year earlier which showed, for example, a similar poorly defined density, superior segment of right lower lobe, with differential diagnosis listing pneumonia, aspiration, and cancer (in sequential order of statistical likelihood).

When correlating these different modalities (of the same anatomic region), the radiologist can conclude that, for example, the chronicity of the finding, interval increase in size, and lack of supportive data to suggest an inflammatory process make carcinoma the primary concern. The corresponding gestures or symbols employed by the radiologist when entering the gestures onto the image using the gesture-based reporting method, denote the following data (in order of application), for example:

1. Density, poorly defined, superior segment right lower lobe, moderate increase in size compared with prior chest CT of Apr. 30, 2004, primary diagnosis carcinoma, high clinical significance, follow-up recommendations: chest CT and oncologic consultation.
2. Cardiomegaly; no changes from preliminary interpretation.
3. Degenerative changes in thoracic spine; no changes from preliminary interpretation.

During the course of the radiologist's review and interpretation, the radiologist can elect to confirm "as is" the findings of cardiomegaly and degenerative changes initially made by the ER physician. This can be done, for example, by placing a "check mark" gesture over the corresponding symbols entered by the ER physician. The radiologist can then modify the gestures or symbols denoting the poorly defined right lower lobe density and then place the image/report in a high priority queue with instructions to electronically page the ER physician for "stat image consultation".

The ER physician can then receive the stat page with the corresponding patient and image/report information. The ER physician can then in turn review the radiologist's interpretation/electronic consultation and return an electronic text message (i.e., high priority) to the radiologist stating they received the consultation, agreed with the interpretation, and have ordered the recommended CT and oncologic consultation.

Of course, an interactive consultation can be initiated if the clinician reviews an image and thinks they see something that the interpreting radiologist missed. In that case, the clinician can record the appropriate gesture (using their own unique color or other identifying format) and electronically send the image to the interpreting radiologist for clarification. By either typing a text message or simply placing a question mark next to the newly added symbol, the radiologist recognizes the clinician's query and can modify the image, and re-send it back to the clinician. This electronic consultation can then be stored in the patient's imaging folder for future reference. All correspondence can take the form of gesture language and be recorded as an additional "layer" of imaging data.

When this image/report is subsequently reviewed by a consulting oncologist, for example, 3 hours later, the oncologist will be able to review any portion or all of the findings made, interpretation, and consultation that ensued. If the oncologist elects to review "all findings", the computer program 110 will present the findings with the initial ER physician's gesture-based report (color coded in a particular color, such as blue, for example), followed by the radiologist's gesture-based report (color coded in a different color, such as red, for example). The oncologist can add any additional findings to the image or incorporate additional clinical/historical data as well.

In this particular example, the oncologist identifies rib destruction (i.e., $4^{th}$ right posterior rib, mild in severity, uncertain diagnostic confidence, high clinical significance). This "questionable discrepancy" is identified by the computer program 110 when inputted by the oncologist and the computer program 110 electronically sends the report to the interpreting radiologist, where it enters a "discrepancy queue" based on this identification.

The radiologist then reviews the oncologist's findings and will send the oncologist a text message, for example, acknowledging the additional findings made, which will be better evaluated on the ordered chest CT. This correspondence (in any format desired, including audio file) may be attached to the image (under the consultation tab, for example) so that the radiologist interpreting the upcoming chest CT will have direct access to the imaging findings and clinical notes of all three physicians involved in the chest radiograph.

These three physicians will in turn automatically receive the chest gesture-based report (with key annotated images) by electronic message. The entire process is easy to accomplish and takes very little time. In fact, the time required for each physician to review their counterpart's findings, enter modification, and initiate the communication protocol should be less than 3 minutes, for example.

In another embodiment consistent with the present invention, the unique signature of the user can be used to define certain privileges in image reporting. This would provide the capability for "second opinions", consultations, and queries, where some users could actively change or delete gestures of other users (i.e., radiologists being able to change or delete gestures of referring clinicians).

For example, a radiology subspecialist may be asked by a primary radiologist, referring clinician, or patient, to review the image and render a "second opinion" or consultation. The consulting radiologist would add or delete gestures to the original report, in doing so, alterations (in the form of gestures or symbols) would be recorded by the program 110 in a different color or other format, so that the user could recognize the distinct nature of the reports of the primary consulting radiologists. Each "individual" report could be selected or activated on an individual basis, with the "final" version of the report (as stored in the imaging archive) recording all versions. When a referring clinician wishes to review an image/report, the program 110 would ask them to select which report to use as the default.

Using this same concept, in another embodiment consistent with the present invention, a clinician could record their own interpreted image findings within their own patient records. An oncologist, for example, may wish to record additional findings not mentioned by the interpreting radiologist. The oncologist would record additional symbols or gestures on the corresponding images and "save" those annotated images as "key images" which go into the patient's oncology folder. These images are then reviewed at the time of the patient's next visit or treatment. When the patient has a follow-up imaging exam (to measure the response to treatment), the annotated images are pulled up (as selected by the oncologist as his/her default), when a query is rendered by the oncologist. The computer (using artificial intelligence as a form of decision support), recognizes the gestures or symbols by the oncologist and highlights the same anatomic region and imaging features on the follow-up exam. This allows the oncologist to serially track imaging findings using their own embedded gestures.

In another embodiment consistent with the present invention, a multi-tiered approach can be taken to the analysis of some radiological data—i.e., mammography. In this embodiment, the RIS and modality would provide the first two tiers of information, whereas the third and fourth tiers would be entered by the radiologist. Further, if NLP were added to the equation, the prior image/report could be pre-screened for pertinent data and presented to the radiologist at the time of interpretation in manner similar to a CAD overlay.

The individual tiers in this embodiment, could be incorporated similar to an Excel spreadsheet, where the user would click on specific tabs of interest. When the "tier 1" tab is clicked, the individual data contained within this tier (i.e., Background Data, such as historical data, clinical indications, historical comparisons), is displayed, along with the ability to directly view the linked historical images. When the "tier 2" tab is activated, the individual data (i.e., Technological Aspects, such as QA descriptors, technique, breast density, and localizing markers), is displayed. This allows the individual radiologist or clinician to customize their viewing protocols as a standard default. All the data is embedded or linked within the image but what is displayed is at the discretion of the individual end user.

"Tier 3" would contain the imaging findings of the radiologist according to the methods and system of the present invention as described above, and "tier 4" is the interpretation, such as the clinical significance of the findings, follow-up recommendations, and confidence in diagnosis. Comparison studies and reports can be electronically linked, and if interpreted using gesture-based reporting, temporal subtraction may be a useful tool over designated areas of pathology.

In other embodiments consistent with the present invention, the following modifications can be made, either in the specific manner that the gesture-based reporting is undertaken, the ancillary technologies used, or the output generated.

For example, potential modifications other than a different input device 104, or a different display device 102, as noted above, would include different gesture or symbol language than identified in the Tables. For example, users will have the capabilities of creating their own unique gestures and symbols, which can in turn be mapped back to the standardized language using translational software. In addition to the proposed graphical language, an alpha numeric symbology could also accomplish the same task, but would be limited by language differences among international users.

As previously mentioned a different output (i.e., report) can be used. The output generated could be customized to the specific preferences of the user. In addition to the graphical display of the images with superimposed gesture-based reporting symbols, the gestures could be mapped to an XML schema with the EMR storing these gestures in a raw format.

Further, there are additional applications of gesture-based reporting outside of Medical Imaging. Gesture-based reporting becomes a viable reporting alternative anywhere the data is presented or recorded in the form of a graphic, diagram, or picture. Medical images are recorded in a number of non-imaging disciplines including (but not limited to) endoscopy, cardiology, ophthalmology, bronchoscopy, dermatology, and colonoscopy. The images obtained are currently stored in the EMR and could easily be used to generate a report using symbols.

For example, the cardiologist performing a coronary angiogram could use gestures or symbols embedded onto the image to describe vascular stenoses (severity, location, clinical significance) and proposed treatment options; all using gesture language. The same cardiologist could also report functional abnormalities (such as cardiac wall motion abnormalities) using gesture language, which could be more easily conveyed than traditional prose reporting.

The ability to identify findings and track interval change electronically (using decision support) is extremely valuable in disciplines such as dermatology, where diagnosis and patient management is largely based on visual input. A dermatologist taking a photograph of a multi-focal rash could use temporal subtraction technology to quantify interval change in number, size, and geographic distribution of the dermatologic condition. Gesture-based reporting could use the gesture or symbol language to identify and describe the pertinent findings and the computer program, could, on follow-up examination, automatically highlight the previously identified areas of abnormality and perform sequential quantitative and qualitative comparison. This allows gesture-based reporting to become a valuable resource for both diagnosis and treatment.

Medical photographs are commonly taken with the operating room to illustrate pathology and these photographs could be easily used in a similar manner. The surgeon would simply superimpose gestures over the area of pathology and use the functionality of the computer workstation to provide magnification and image processing to enhance areas of concern. The anatomic relationship of the area of pathology to surrounding normal tissue and organs is best depicted using medical photography and gesture-based reporting becomes the logical means of reporting.

In addition to the "macroscopic" photos taken intra-operatively, "microscopic" photos are commonly used by pathologists and would be well suited for gesture-based reporting. In pathology, the boundaries between normal and abnormal cells is especially critical and text reports are difficult to communicate these subtleties. A magnification view of a specially stained microscopic specimen would both delineate these boundaries between normal and abnormal and specifically identify abnormal cells. The specific abnormalities of these individual cells can be highlighted and reported using gesture-based symbols, which again would be standardized. This would be beneficial in pathology where consultations with "outside experts' are frequently sought. The ability to electronically transmit the micro and macroscopic images with highlighted findings using a standardized gesture or symbol language is particularly appealing.

Further, a variety of medical notes currently written in text format could be easily converted to gesture-based reporting format, using gestures superimposed upon diagrams. For instance, a physician recording a history and physical could use symbols superimposed upon computer generated diagrams of each respective organ system to record pertinent findings and the associated modifying terms and concepts previously described. The same principles can be applied to procedure notes, consultations, and progress notes.

Another category of medical reports for gesture-based reporting application are existing tests displayed in graphical representation (EEG, EMG, EKG). The neurologist interpreting an EEG could highlight "key portions" of the graphical display that correspond to abnormal findings and annotate these findings using gesture-based reporting. These key portions of the graphical analysis highlighted are then stored by the computer program separate from the comprehensive dataset and used for detailed comparison on follow-up exams. The same applications of decision support can be used in conjunction with gesture-based reporting for interpretation and reporting.

A number of non-medical applications would be well suited for gesture-based reporting, which include anything that is predicated upon pictorial or graphical representation. A policeman or insurance adjustor investigating a traffic accident can use graphical representation of the accident scene, automobiles, and ensuing damage through a series of photographs and diagrams which can in turn be annotated with gestures or symbols for reporting. Similar applications can be used for engineering, design, and architectural professionals.

In order to address these divergent needs and expectations of generalists and specialists in the medical profession, a two-tiered gesture-based reporting language can be used with equal proficiency among general radiologists and subspecialty radiologists. The basic set of gestures or symbols (see Tables 1-2) would be applicable to a number of commonly observed radiological findings, and be common to all imaging modalities and anatomic regions. The specialized set of gesture-based reporting symbols would be more granular in nature and specialized to different organ systems and imaging modalities. Lack of knowledge of the specialized set of symbols would not preclude one's ability to use gesture-based reporting methods and systems as illustrated below.

In this example, two different radiologists are using gesture-based reporting in the interpretation of a brain CT in, for example, an 8-year old boy with vomiting and headaches. The general radiologist identifies a mass in the posterior fossa of the brain and highlights the "key images". While going through the gesture-based reporting process of describing the unidentified mass, the radiologist describes it with the following descriptors: mass, poorly defined, cerebellum, minimal mass effect, high clinical significance, uncertain etiology, follow-up recommendation for MRI.

The neuroradiologist interpreting the same study also uses gesture-based reporting but describes the mass in slightly different terms: mass, cerebellar vermis, well defined associated hydrocephalous, internal cystic change and calcification, high clinical significance, medulloblastoma, neurosurgical consultation.

Using decision support and additional information obtained from the EMR, the computer program 110 of the present invention, using neural networks that are preprogrammed into the software, will ask the general radiologist a few targeted questions for improved characterization. The program 110 first asks the radiologist to localize the mass using the anatomic map. In doing so, a corresponding reference brain CT is brought up by the program 110, and the radiologist places his/her stylus over the exact area of the mass in question. The computer program 110 then clarifies the anatomic location as "cerebellar vermis".

The second question the computer program 110 asks is, "is there associated hydrocephalous?" The radiologist reviews the images and answers "yes". The third question posed by the computer program 110 is" does this mass contain any internal calcification, hemorrhage, or cystic change?'. The radiologist points the stylus 104 over both cystic change and calcification to denote its presence. The computer 110 (using neural networks) identifies the mass in question as a medulloblastoma and presents the radiologist with teaching file cases from an electronic database.

When asked by the computer program 110 if these images correspond to the clinical entity in question, the radiologist answers "yes" and enters this as the presumptive diagnosis with a "high degree of clinical confidence".

The end result is the gesture-based language used to describe the mass is almost identical in the final report for both radiologists. The path in which they took may have been slightly different, but the end result and corresponding report is similar. In addition to incorporating decision support into the gesture-based reporting interpretation process, educational feedback on the gesture or symbol language is also provided to end users for continued learning.

The learning process for use of the gesture-based reporting method and system is also bidirectional in nature. The end user must learn the gesture or symbol language and descriptive methodology while the computer program 110 learns to accurately comprehend the gestures or symbols uniquely created by each end user. This process of iterative learning by the computer program 110 in gesture recognition is similar to that currently employed with speech recognition technology. In one example consistent with the present invention, when the radiologist recognizes the computer program 110 has incorrectly identified the symbol entered, he/she clicks on the "learning icon". The computer program 110 than asks for the end user to draw the desired symbol three times and asks the user to map it to the corresponding text.

In one embodiment consistent with the present invention, the computer program 110 also tracks the frequency with which each individual gesture or symbol is used by each radiologist and creates a statistical profile of most commonly used gestures or symbols. Collectively this allows the computer program 110 to enhance its accuracy in gesture recognition.

End user education can be provided through a number of means including, for example, on-line learning which teaches the radiologist commonly used gestures or symbols and how to create user-specific symbols. The computer program 110 may also provide a library of standardized gestures or symbols (with corresponding text) that can be used by "touching and dragging" the desired gesture or symbol to the image, using the stylus 104. Since not all concepts may be able to be described by gestures alone, for these instances an alternative input (speech or pull-down menus) can be included in the reporting system 100.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A computer-implemented method of image reporting comprising:
   displaying an image;
   detecting a pre-defined first symbol that is drawn on the displayed image by a user with an input device;
   performing symbol recognition to identify the first symbol;
   correlating the first symbol to a first predetermined information;
   displaying the image with the first symbol disposed on the image; and
   associating said image with at least one of the first symbol and the first predetermined information; and
   generating a comprehensive textual report by mapping said first symbol into a hierarchical input database.

2. The method according to claim 1, further comprising:
   detecting a second pre-defined symbol that is drawn on the displayed image by the user with the input device;
   performing symbol recognition to identify the second symbol;
   correlating the second symbol to second predetermined information;
   displaying the image with the second symbol disposed on the image; and
   associating the image with at least one of the second symbol and the second predetermined information.

3. The method according to claim 2, wherein said second symbol is a modifier symbol.

4. The method according to claim 3, further comprising:
   providing said image from a plurality of images in an image study.

5. The method according to claim 4, wherein said image study is provided for viewing in one of a static and a dynamic fashion.

6. The method according to claim 5, further comprising showing the first symbol and the second symbol on said image in an order applied by a user.

7. The method according to claim 4, wherein at least one of the first symbol and the second symbol is transferable from said image to another image in said image study.

8. The method according to claim 4, further comprising storing images with the symbols thereon as key images separately from other images in said image study.

9. The method according to claim 8, further comprising displaying said key images in a pre-selected user format, which includes pre-selected variables.

10. The method according to claim 3, wherein at least one of the first predetermined information and the second predetermined information corresponds to a pathology in a medical application.

11. The method according to claim 10, wherein said modifier symbol identifies and quantifies said pathology.

12. The method according to claim 10, wherein said medical application is radiology.

13. The method according to claim 3, further comprising:
    providing text correlating to at least one of the first predetermined information and the second predetermined information, wherein the text is positioned proximate to said at least one of said first symbol and said second symbol; and
    confirming that said text correctly denotes said at least one of said first symbol and said second symbol.

14. The method according to claim 13, further comprising:
    deleting said text and said corresponding symbol in response to a user command, when said text does not correctly denote said corresponding symbol.

15. The method according to claim 13, further comprising:
    forwarding said image with at least one of the first symbol and the second symbol disposed thereon, to a selected user.

16. The method according to claim 15, further comprising:
    generating a report on said image having said first and second symbols.

17. The method according to claim 16, further comprising:
    generating another image by placing the symbols from the report on said another image.

18. The method according to claim 17, further comprising:
    generating a plurality of reports with symbols provided in differing formats and colors, wherein the symbols are overlaid on said another image with previously placed symbols.

19. The method according to claim 18, wherein temporal subtraction is applied to said plurality of reports to show changes in said another image.

20. The method according to claim 18, further comprising:
    obtaining a signature of the user that accesses at least one of the image and reports; and associating the signature with at least one of the accessed image and reports.

21. The method according to claim 20, further comprising sorting said reports by said signature of said user associated with said image.

22. The method according to claim 20, further comprising:
    assigning editing privileges to each user that accesses at least one of the image and the reports based at least on the signature provided by the user; and
    enabling each user to perform actions on the at least one of the image or the reports based on the assigned editing privileges.

23. The method according to claim 3, further comprising:
    applying automated decision support systems to interpret said image.

24. The method according to claim 23, wherein the automated decision support systems provide findings and wherein the findings are disposed on said image as symbols in one of a format and a color which differs in visual appearance from said previously disposed symbols.

25. The method according to claim 23, wherein applying automated decision support systems include applying neural networks to further define and interpret said image.

26. The method according to claim 3, further comprising:
    providing additional data to a user to assist in image interpretation.

27. The method according to claim 2, further comprising:
tracking a frequency of use of at least one of the first symbol and the second symbol that is applied to said image; and
creating a statistical profile of commonly used symbols to enhance accuracy of symbol recognition.

28. The method according to claim 1, wherein said input device is a programmable stylus.

29. The method according to claim 1, further comprising:
searching a database of said image having the symbols stored thereon, for a selected symbol.

30. The method according to claim 1, wherein said first symbol is one of a graphic and a numerical representation.

31. The method according to claim 1, wherein said image includes at least one of an x-ray, a digital representation, a photograph, a graphical representation, a blueprint, and a medical printout.

32. The method according to claim 1, wherein said displaying step is performed by a picture archiving and communication system.

33. The method according to claim 1, wherein said associating step is performed by a picture archiving and communication system.

34. The method according to claim 1, wherein said display is one of a touch screen, and a pair of goggles.

35. A computer system having a program for performing image reporting, comprising:
means for displaying an image;
means for drawing a pre-defined first symbol onto the displayed image, wherein said drawing is performed by a user;
means for detecting the first symbol that is drawn on the displayed image;
means for performing symbol recognition to identify the first symbol;
means for correlating the first symbol to first predetermined information;
means for displaying the image with the first symbol disposed on the image; and
means for associating said image with at least one of the first symbol and the first predetermined information; and
means for generating a comprehensive textual report by mapping said first symbol into a hierarchical input database.

36. The computer system of claim 35, further comprising:
means for drawing a second pre-defined symbol on the display image, wherein said drawing is performed by a user;
means for detecting the second symbol that is drawn on the displayed image;
means for performing symbol recognition to identify the second symbol;
means for correlating the second symbol to second predetermined information;
means for displaying the image with the second symbol disposed on the image; and
means for associating the image with at least one of the second symbol and the second predetermined information; and
means for generating a comprehensive textual report by mapping said second symbol into a hierarchical input database.

37. The computer system of claim 36, further comprising:
means for forwarding said image with at least one of the first symbol and the second symbol disposed thereon, to a selected user.

38. The computer system according to claim 37, further comprising:
means for applying automated decision support systems to interpret said image.

39. The computer system according to claim 37, further comprising:
means for generating a report on said image having said first symbol.

40. The computer system according to claim 39, further comprising:
means for generating another image by placing the symbols from the report, on said another image.

41. The computer system according to claim 40, further comprising:
means for providing additional data to a user to assist in image interpretation.

42. The computer system according to claim 41, further comprising:
means for tracking a frequency of use of the first symbol that is applied to said image; and
means for creating a statistical profile of commonly used symbols to enhance accuracy of symbol recognition.

43. A computer system for performing image reporting, comprising:
at least one memory containing at least one program comprising the steps of:
displaying an image;
detecting a pre-defined first symbol that is drawn on the displayed image using an input device, wherein the first symbol is drawn by a user;
performing symbol recognition to identify the first symbol;
correlating the first symbol to first predetermined information;
displaying the image with the first symbol disposed on the image; and
associating said image with at least one of the first symbol and the first predetermined information; and
generating a comprehensive textual report by mapping said first symbol into a hierarchical input database; and
at least one processor for running the program.

44. An apparatus for performing image reporting, comprising:
a display, which displays an image;
an input device that enables a user to draw at least one pre-defined symbol on said displayed image;
a processor that enables detection of the at least one symbol performs symbol recognition to identify the at least one symbol, correlates the at least one symbol to predetermined information, enables display of the image with the at least one symbol drawn on said displayed image, enables association of said image with at least one of the at least one symbol and the predetermined information, and generates a comprehensive textual report by mapping said symbol into a hierarchical input database.

45. The apparatus according to claim 44, wherein said input device is a programmable stylus.

46. The apparatus according to claim 44, further comprising:
an automated decision support system that interprets said image.

47. The apparatus according to claim 44, wherein said display is a touch screen monitor.

48. The apparatus according to claim 44, wherein said display is part of a picture archiving and communication system.

49. The apparatus according to claim 44, wherein said processor communicates with a picture archiving and communication system.

50. The apparatus according to claim 44, wherein the processor associates the at least one pre-defined symbol with corresponding text.

51. A computer-readable medium whose contents cause a computer system to perform image reporting, the computer system having a program comprising the steps of:
displaying an image;
detecting a pre-defined first symbol that is drawn on the displayed image by a user with an input device;
performing symbol recognition to identify the first symbol;
correlating the first symbol to first predetermined information;
displaying the image with the first symbol disposed on the image;
associating said image with at least one of the first symbol and the first predetermined information; and
generating a comprehensive textual report by mapping said first symbol into a hierarchical database.

52. A computer-implemented method of image reporting in a medical application, comprising:
displaying an image;
detecting a pre-defined first symbol that is drawn on the displayed image by a user with an input device;
performing symbol recognition to identify the first symbol;
correlating the first symbol to first predetermined information;
displaying the image with the first symbol disposed on the image;
associating said image with at least one of the first symbol and the first predetermined information; and
generating a comprehensive textual report by mapping said first symbol into a hierarchical input database.

53. The method according to claim 52, further comprising:
detecting a pre-defined second symbol that is drawn on the displayed image by the user with the input device;
performing symbol recognition to identify the second symbol;
correlating the second symbol to second predetermined information;
displaying the image with the second symbol disposed on the image; and
associating the image with at least one of the second symbol and the second predetermined information.

54. The method according to claim 53, further comprising:
generating a report on said image having said first and second symbols.

55. A method of performing electronic consultation between at least two users, comprising:
displaying an image;
enabling a first user to draw a pre-defined first symbol that corresponds to first predetermined information on the displayed image;
forwarding said image with said symbol to at least a second user;
enabling a second user to draw a pre-defined second symbol that corresponds to second predetermined information on the displayed image having the first symbol disposed thereon;
forwarding said image with the at least second symbol from said at least second user to said first user;
enabling modification of at least one of the first symbol and the second symbol by said first user;
forwarding said image back to said at least second user; and
generating a comprehensive textual report by mapping said at least one of the first and second symbols into a hierarchical input database.

56. A method of performing electronic consultation between at least two users, comprising:
displaying an image;
enabling a first user to draw a pre-defined first symbol that corresponds to first predetermined information on the displayed image;
forwarding a first message to at least a second user requesting review of the image with the disposed first symbol;
enabling the at least second user to access the first message, display the image and draw a pre-defined second symbol that corresponds to second predetermined information on the displayed image having the first symbol;
forwarding a second message to the first user requesting review of the image with the first and second symbols; and
generating a comprehensive textual report by mapping said first and second symbols into a hierarchical input database.

57. The method according to claim 56, wherein the first message is auto-routed to the at least second user using a pre-defined communication protocol.

58. A method of image reporting comprising:
displaying a plurality of images;
detecting a pre-defined symbol that is drawn on the displayed plurality of images by a user with an input device;
performing symbol recognition to identify the symbol;
correlating the symbol to predetermined information;
displaying the plurality of images with the symbol disposed thereon;
tracking a frequency with which the symbol is detected;
creating a statistical profile based on the frequency with which the symbol is detected; and
applying the statistical profile to enhance an accuracy of recognizing the symbol;
generating a comprehensive textual report by mapping said symbol into a hierarchical input database.

59. The method according to claim 58, wherein the statistical profile is associated with a user profile.

* * * * *